United States Patent [19]

Holtkamp

[11] Plant 4,266

[45] Jun. 20, 1978

[54] AFRICAN VIOLET PLANT

[76] Inventor: Reinhold Holtkamp, Wertherstrasse 112, 4294 Isselburg, Germany

[21] Appl. No.: 746,216

[22] Filed: Nov. 30, 1976

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet plant having purplish-red flower color, frilled petal edges, vigorous and compact growth, upright and strong flower stems, profuse blooming and long blooming period.

1 Drawing Figure

1

The present invention comprises a new and distinct cultivar of African violet plant, botanically known as *Saintpaulia ionantha,* and hereinafter referred to by the cultivar name Colorado.

Colorado, referred to during the selection process by the designation (b. 16/9) 63/76 red frilled is the product of a planned breeding program which had the objective of creating a new African violet cultivar having a combination of certain of the proven characteristics of the parent cultivars. The female, or seed parent, is designated as f III pink frilled, color 43-1, and was selected for breeding because of its frilled edges of the flower petals. The male, or pollen parent, is designated XIX 4395 pink star, color 43-3, and was selected for breeding due to its upright flower stems and excellent array of leaves surrounding the flower bouquet. The new cultivar was originated from a cross made by me in Isselburg, West Germany, and was selected as a flowering plant from the progeny of the stated cross in a controlled environment in Isselburg, West Germany. Colorado possesses the desired characteristics of its parents and has a generally purplish-red flower color, as contrasted to the pink flower color of both of its parents.

Asexual reproduction of the new cultivar by leaf cuttings and by division of shoots, as performed by me at Isselburg, Rhineland, Germany has demonstrated that the combination of characteristics as herein disclosed for the new cultivar are firmly fixed and are retained through successive generations of asexual reproduction.

The following observations, measurements and values describe plants grown in Isselburg, Rhineland, Germany under greenhouse conditions which closely approximate those generally used in commercial practice.

The following traits have been repeatedly observed and are determined to be basic characteristics of Colorado, which in combination distinguish this African violet as a new and distinct cultivar:

1. Large flowers with frilled edges, wherein the flowers do not fade and drop.
2. Purplish-red flower color.
3. Profuse flowering on strong stems, and long blooming period.
4. Vigorous growth with upright flower stems.
5. An attractive saleable plant is present at first flash of flowers.
6. Compact habit.

The accompanying photographic drawing shows a typical specimen plant of the new cultivar. The colors

2 appearing in the photograph are as true as possible with color illustrations of this type.

In the following description, color references are made to the Munsell Limit Color Cascade chart, except where general color terms of ordinary significance are indicated.

Botanical classification: *Saintpaulia ionantha,* Ramat. cv Colorado.

Parentage:

*Male parent.*—XIX 4395, pink star.

*Female parent.*—f III, pink, frilled.

Propagation: The new cultivar holds its distinguishing characteristics through successive propagations by leaf cuttings and by division of shoots.

Plant:

*Size.*—From 7 cm. to 10 cm. tall when grown in pots, and approximately 25 cm. in diameter when fully grown.

*Leaves.*—General Form: oval. Diameter: 45–60 mm. Texture: soft, hairy. Aspect: velvety. Veins: underside, well pronounced. Color: upperside — dark green 19-15. underside — dark brown-red.

*Flowers.*—Buds: Ball-shaped, approximately 8–10 mm. before opening; generally purplish-red in color. Sepals: Five, two small, three large, all frilled. Color: Purplish-red. Calyx: Funnel-shaped. Aspect: Spear-shaped. Peduncle: brown-red, strong, upright, 2–3 cm.

*Individual flowers.*—Size: 40–50 mm. Color: Upperside — 46-10. Underside — 45-13. Borne: Every flower stem has 7–9 flowers on strong peduncles. Shape: Five petals, 2 small and 3 large with frilled edge. Corolla: The large petals are 27 mm. long and 22 mm. wide; the small petals are 22 mm. long and 22 mm. wide. Arrangement: Strong and upright peduncles with up to 9 large flowers. Flowering time: Approximately 6–7 weeks after potting the first flowers appear and 3 weeks more to full flower.

*Reproductive organs.*—Anthers: two, 4 mm.; color 27-4, golden yellow, seed capsule pushes slightly through. Arrangement: basifixed. Filaments: 3–4 mm. long, green yellow, middle part brown-violet. Styles: base light green, hairy; upper part red violet, color 44-12. Pollen color: 27-2.

*Roots.*—Well developed root system, white when young and active.

*Disease Resistance.*—Very good.

General observations: Colorado is a unique cultivar and provides for the first time an African violet having intensive red-purple flower color and frilled petal edges. The flowers are carried on strong, upright stems, and the flower color does not fade on maturity, nor do the petals drop. The flowering is profuse and the blooming period relatively long, and although Colorado does not continuously bloom, there are second and further blooming periods at approximately 7–8 week intervals, and the subsequent flowerings are even more attractive than the original flowering, with the flowers being relatively larger in diameter and more intensive in color.

I claim:

1. A new and distinct cultivar of African violet plant known by the cultivar name Colorado and characterized as to novelty by the combined characteristics of purplish-red flower color, frilled petal edges, vigorous and compact growth, upright and strong flower stems, profuse blooming and long blooming period.

* * * * *

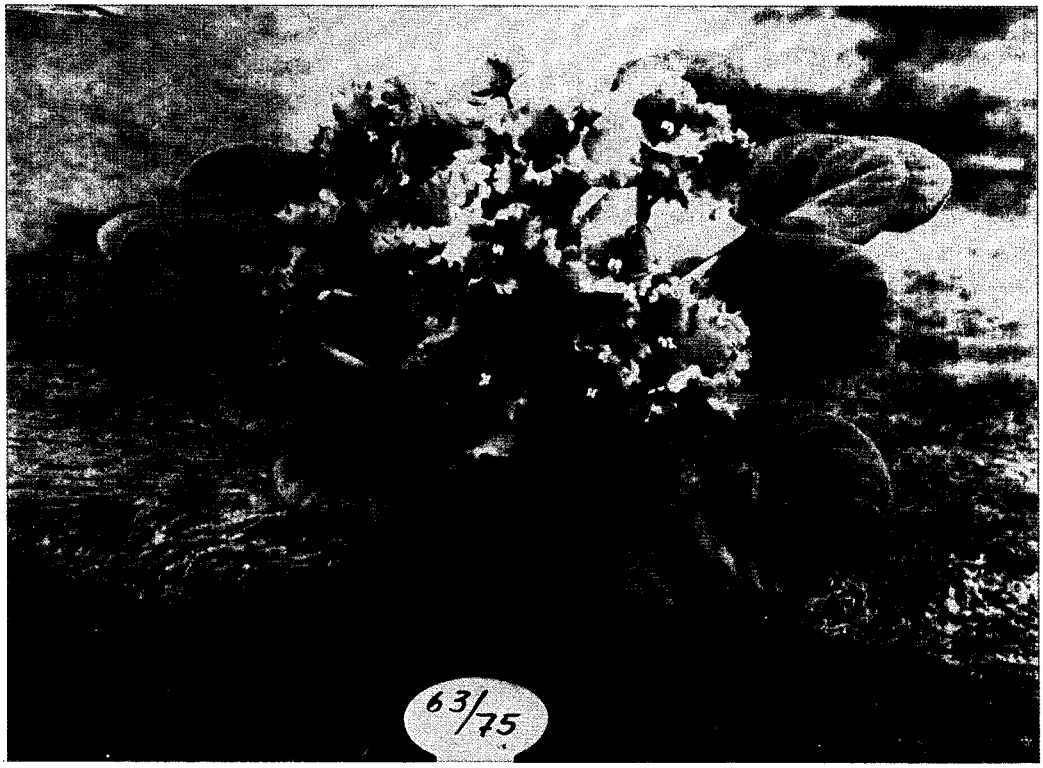
63/75